United States Patent [19]

Hope

[11] Plant 4,343

[45] Dec. 12, 1978

[54] KALANCHOE PLANT NAMED GODDESS

[75] Inventor: Claude Hope, Cartago, Costa Rica

[73] Assignee: Pan-American Plant Company, West Chicago, Ill.

[21] Appl. No.: 876,428

[22] Filed: Feb. 9, 1978

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A new variety of kalanchoe plant intended for greenhouse culture as a pot plant and suitable for year around flowering with photoperiod control, characterized by the intense rose pink color of its florets which range from 10 to 12 mm. in diameter, a uniform 10-week flowering response, a medium plant height and an extended blooming period due to several weeks of continuous flower bud development.

1 Drawing Figure

BACKGROUND OF THE NEW PLANT

My new variety of kalanchoe plant originated as a seedling resulting from my crossing Swiss Rose (unpatented) with Red Empress (unpatented) as the pollen parent, in my breeding facilities at Cartago, Costa Rica, in the course of breeding efforts carried on by me since 1969. Asexual propagation of this plant by vegetative cuttings, done by me at Cartago, Costa Rica, and carried through successive generations, has demonstrated that its distinctive characteristics hold true from generation to generation and appear to be firmly fixed. Commercial scale propagation of this new plant by means of cuttings is now being done at Cortez, Fla., and at West Chicago, Ill.

DESCRIPTION OF THE DRAWING

My new kalanchoe plant is illustrated by the accompanying drawing which shows the growth and flower display characteristics of the plant, as well as the flower color, the drawing having been made by conventional full-color photographic procedures and the color shown being as nearly true as it is reasonably possible to obtain in that manner.

DESCRIPTION OF THE NEW PLANT

The following is a detailed description of my new variety of kalanchoe plant with color designations according to the R.H.S. Colour Chart published by The Royal Horticultural Society of London, England, in collaboration with the British Colour Council.

THE PLANT

Origin: Seedling.
Parentage:
- *Seed parent.*—Swiss Rose (unpatented).
- *Pollen parent.*—Red Empress (unpatented).

Classification:
- *Botanic.*—*Kalanchoe blossfeldiana.*
- *Commercial.*—Kalanchoe pot plant.

Form: Upright bush.
Height: 17 to 22 cm.
Growth: Sturdy and strong with medium vigor.
Branching: Normal under natural conditions.
Foliage:
- *Leaf size.*—Medium, about 5.5 to 12 cm. long and about 3.0 to 5.5 cm. wide.

- *Shape.*—Elliptical, with obtuse tip and dentate margins.
- *Texture.*—Thick, fleshy and smooth.
- *Surface aspect.*—Glossy.
- *Color.*—Upper side — 146A. Under side — 146B.
- *Venation.*—Pinnate.
- *Petioles.*—14 to 30 mm. long.

THE BUD

Shape: Generally cylindrical with a somewhat pointed tip before opening.
Size:
- *Diameter.*—About 1.75 mm.
- *Length.*—About 6 to 7 mm.

Opening rate: Fast, opens fully within 1 day.
Sepals: Four or five sepals surround the receptacle.
- *Appearance.*—Upstanding and spear-shaped.
- *Surface texture.*—Smooth.
- *Aspect.*—Shiny.
- *Color.*—Inside — 144A. Outside — 144A.

THE FLOWER

Flowering: 10-week response with photoperiod control. Can be flowered year around.
- *Natural season.*—November through January under Costa Rican environments.

Blooms: Flower type — Regular and complete.
- *Borne.*—On a compound cyme.
- *Size.*—Small — About 10 to 12 mm. in diameter and about 8 to 10 mm. in depth.
- *Shape.*—Generally flat when bloom first opens, petals becoming reflexed as flower matures.
- *Petals.*—Four to five per flower, separate and distinct.
- *Form.*—Nearly oval, about 5 mm. long and about 3.5 mm. wide.
- *Texture.*—Firm.
- *Appearance.*—Shiny.
- *Color.*—Upper Side — 57B with 46C at base. Under Side — 55C.
- *Tonality of florescence at a distance of 8 feet.*—52A.
- *Discoloration.*—Moderate fade after full bloom.

Peduncle: Sturdy and upright.
- *Surface texture.*—Smooth.
- *Color.*—146C and 199A.

Persistence: Flowers hang on and dry.

Effect of weather: None. Recommended only for greenhouse culture.

Disease resistance: This plant has been observed to resist powdery mildew in environments where that disease is present.

Fragrance: Typical kalanchoe.

Lasting quality: Approximately 4 weeks.

REPRODUCTIVE ORGANS

Stamens: Number 8 to 10.

*Anthers.*—Color — Yellow.

*Filaments.*—Color — Yellow-Green.

*Pollen.*—Color — Yellow.

Pistils: Number four or five.

*Stigmas.*—Color — Initially Yellow-Green, turning to Off-White as flower ages.

*Ovaries.*—Number four or five, each developing multiple seeds.

My new kalanchoe plant is particularly distinguished by its very attractive rose-pink florets which range from about 10 to 12 mm. in diameter in size and bloom continuously over an extended blooming period because of continuous flower bud development. This plant can be flowered the year around under photoperiod control and has a uniform 10-week flowering response. It grows rapidly with a medium plant height when flowering and has attractive, medium sized, glossy foliage.

The kalanchoe "Goddess" herein shown and described is a sister plant to the variety "Toltec" disclosed and claimed in my co-pending application Ser. No. 876,429, filed of even date herewith, both plants having been bred from the same parents. The following table is intended to show the differences between the two plants.

| Plant: | "Goddess" | "Toltec" |
|---|---|---|
| Height: | 17–22 Cm. | 18–26 Cm. |
| Growth: | Strong with medium vigor. | Good strength; medium vigor. |
| Branching: | Normal | Normal |
| Foliage: | | |
| Size of Leaf: | | |
| Length: | 5.5–12 Cm. | 5.5–11 Cm. |
| Width: | 3–5.5 Cm. | 3.5–5 Cm. |
| Shape of Leaf: | Elliptical | Ovate |
| Color: | | |
| Upper Side: | 146A | 147A |
| Under Side: | 146B | 147B |
| Florescence: | | |
| Response: | 10-week | 10-week |
| Bud Size: | | |
| Diameter: | 1.75 mm. | 1.75 mm. |
| Length: | 6–7 mm. | 9–11 mm. |
| Flower Size: | | |
| Diameter: | 10–12 mm. | 10–12 mm. |
| Depth: | 8–10 mm. | 9–11 mm. |
| Borne: | On a compound cyme. | Corymbos on a compound cyme. |
| Color of Petals: | | |
| Upper Side: | 57B–46C at base. | 40A and 42A; base 1A. |
| Under Side: | 55C | 39B and 179C |
| Tonality at 8 Ft.: | 52A | 41A |

I claim:

1. A new and distinct kalanchoe cultivar, substantially as herein shown and described, characterized by its upright growth of medium height, its substantially uniform 10-week flowering response under photoperiod control, and its continuous and showy production of rose pink flowers over an extended blooming period.

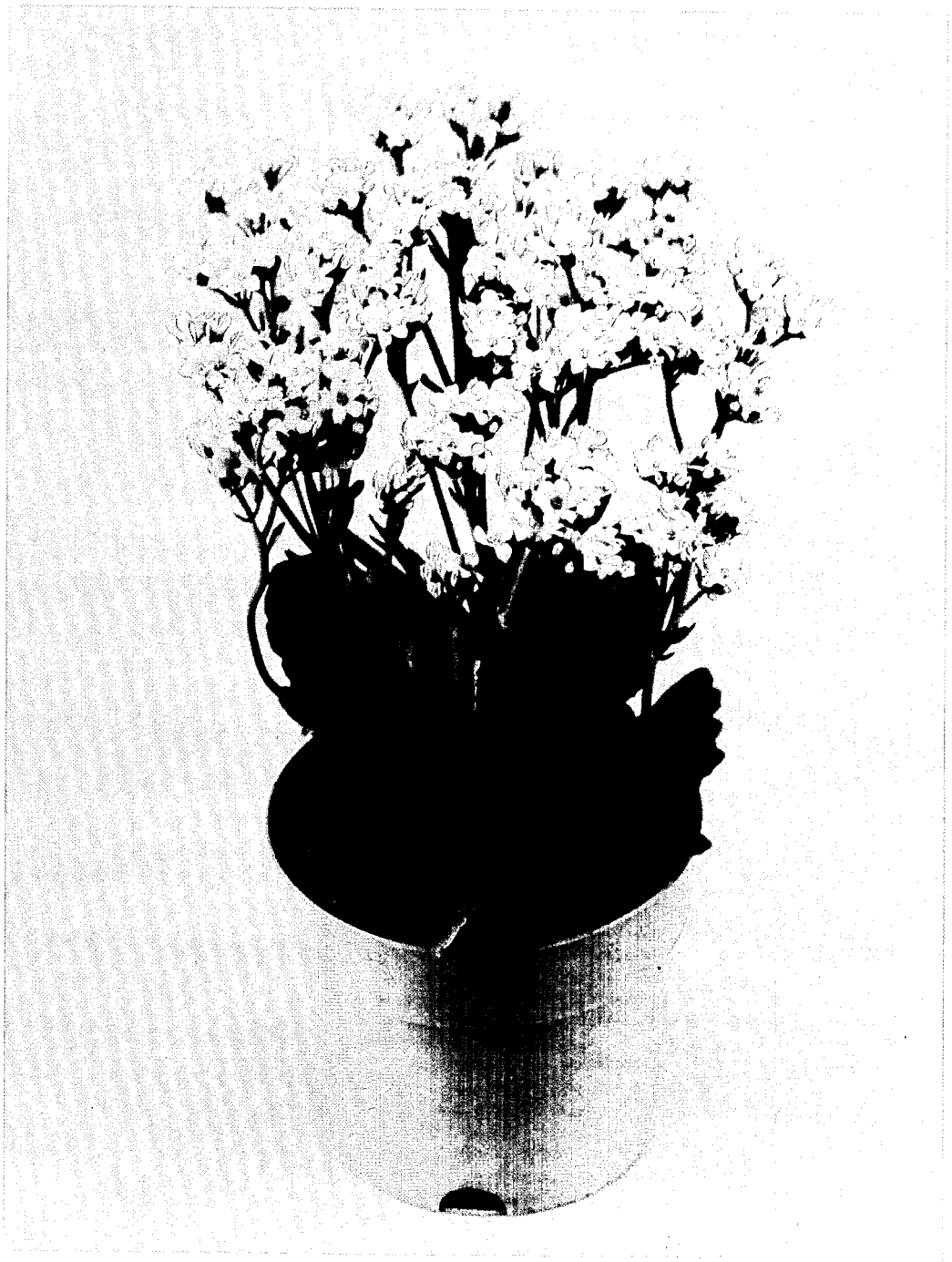

* * * * *